(12) United States Patent
Lee et al.

(10) Patent No.: US 10,781,521 B2
(45) Date of Patent: Sep. 22, 2020

(54) PREPARATION METHOD OF DUAL LAYERED COATINGS ON MAGNESIUM ALLOYS WITH FLUORINE/POLYCAPROLACTONE FOR BIOMEDICAL APPLICATIONS

(71) Applicant: Soonchunhyang University Industry Academy Cooperation Foundation, Asan-si (KR)

(72) Inventors: Byong Taek Lee, Cheonan-si (KR); Gun Hee Lee, Cheonan-si (KR); Preeti Makkar, Cheonan-si (KR)

(73) Assignee: SOONCHUNHYANG UNIVERSITY INDUSTRY ACADEMY COOPERATION FOUNDATION, Asan-si (KR)

( * ) Notice: Subject to any disclaimer, the term of this patent is extended or adjusted under 35 U.S.C. 154(b) by 146 days.

(21) Appl. No.: 15/986,995

(22) Filed: May 23, 2018

(65) Prior Publication Data
US 2019/0024244 A1 Jan. 24, 2019

(30) Foreign Application Priority Data
Jul. 19, 2017 (KR) .................. 10-2017-0091697

(51) Int. Cl.
| | | |
|---|---|---|
| C23C 30/00 | (2006.01) | |
| C23C 8/42 | (2006.01) | |
| A61L 27/30 | (2006.01) | |
| A61L 27/34 | (2006.01) | |
| A61L 27/04 | (2006.01) | |
| C23C 28/00 | (2006.01) | |
| A61L 27/58 | (2006.01) | |
| C22C 23/04 | (2006.01) | |
| C23C 8/02 | (2006.01) | |

(52) U.S. Cl.
CPC ............ *C23C 30/00* (2013.01); *A61L 27/047* (2013.01); *A61L 27/306* (2013.01); *A61L 27/34* (2013.01); *A61L 27/58* (2013.01); *C23C 8/42* (2013.01); *C23C 28/00* (2013.01); *A61L 2420/02* (2013.01); *A61L 2420/08* (2013.01); *A61L 2430/02* (2013.01); *C22C 23/04* (2013.01); *C23C 8/02* (2013.01)

(58) Field of Classification Search
CPC . C23C 30/00; C23C 8/42; A61L 27/34; A61L 27/047; A61L 27/306
See application file for complete search history.

(56) References Cited

FOREIGN PATENT DOCUMENTS

KR 10-2009-0067871 6/2009

*Primary Examiner* — Jessee R Roe
(74) *Attorney, Agent, or Firm* — Lex IP Meister, PLLC (57) ABSTRACT

The present invention relates to a method for preparing a dual-layer magnesium alloy with fluoride and biopolymer coatings, wherein the dual-layer $MgF_2$/PCL coating exhibits improved corrosion resistance as compared to fluoride-coated samples or uncoated Mg samples, and has excellent cell viability, cell adhesion and cell proliferation. Accordingly, the magnesium alloy provided with the dual $MgF_2$/PCL coating layer controls corrosion degradation of conventional orthopedic Mg alloys and exhibits excellent biocompatibility, thus being useful as an implant for fixing bones.

7 Claims, 10 Drawing Sheets

PREPARATION METHOD OF DUAL LAYERED COATINGS ON MAGNESIUM ALLOYS WITH FLUORINE/POLYCAPROLACTONE FOR BIOMEDICAL APPLICATIONS

BACKGROUND OF THE INVENTION

Field of the Invention

The present invention relates to a method for preparing a dual-layer coating on magnesium alloy with improved corrosion resistance, and application of the dual-layer coated magnesium alloy to implants for bone grafting.

Description of the Related Art

Biodegradable metals have received a great deal of attention in recent times due to applications thereof as orthopedic implants and cardiovascular interventional devices. Biodegradable metals are attractive alternatives due to their higher load-bearing capacity and lower material cost compared to polymeric counterparts.

Since bone fracture during bone treatment should maintain mechanical integrity and biocompatibility, metal implants are needed to fix bone fracture. For this purpose, titanium, stainless steel, cobalt, chromium and nickel substrates have many drawbacks. As modulus of elasticity of these orthopedic metals increases, stress shielding effects occurs on the bone, resulting in osteopenia and the like. Implants, except titanium, produce toxic corrosion products, causing inflammation and allergic reaction. Titanium is a non-toxic implant candidate material, but long-term implantation causes electrochemical corrosion and loosening of implants, resulting in inflammatory response and thus requiring secondary surgeries for removal of implants. Secondary surgeries increase the risk of infection and financial burden.

Meanwhile, magnesium (Mg) and alloys thereof have similar density, modulus and compressive yield strength to human bone and a unique property of being degradable in vivo. Such very similar mechanical properties to the human body can minimize stress shielding effects caused by the difference in elastic modulus between foreign implants and host hard tissues. However, non-homogenous and rapid corrosion with hydrogen gas release and increased alkaline pH in the vicinity of the implant have limited their clinical application.

Accordingly, there is a need for improvement in corrosion resistance of magnesium alloys.

PRIOR ART

Patent Document (Patent Document) Korean Patent No. 10-0971248

SUMMARY OF THE INVENTION

As a result of thorough and extended efforts to develop methods capable of improving corrosion resistance of magnesium alloys as bone implants, the present inventors completed the present invention, based on the finding that corrosion resistance of magnesium alloys can be improved and excellent cell viability, cell adhesion and proliferation can be obtained by fluoride and biopolymer coating.

The present inventors conducted dual-coating of biodegradable magnesium alloys with biodegradable $MgF_2$/PCL, analyzed properties such as morphology of the dual coating, elemental profile, phase structure, roughness, mechanical properties, in vitro corrosion and biocompatibility, and compared these properties with those of fluoride coated samples and non-coated Mg samples. Results revealed that the dual-layer coating is uniform and consists of dense $MgF_2$ (~2.2 μm) as an inner layer and a porous PCL membrane (~3.3 μm) as an outer layer, and the dual-layer $MgF_2$/PCL coating exhibits improved corrosion resistance as compared to monolayer $MgF_2$ or Mg alloy alone, and has excellent cell viability, cell adhesion and cell proliferation and that the magnesium alloy with the dual $MgF_2$/PCL coating layer controls corrosion degradation of conventional orthopedic Mg alloys and exhibits excellent biocompatibility, thus being useful as an implant for fixing bones. Based on these findings, the present invention has been completed.

In accordance with the present invention, the above and other objects can be accomplished by the provision of a method for preparing a dual-layer coating on magnesium alloy with improved corrosion resistance including polishing the surface of a magnesium alloy, treating the polished magnesium alloy with fluoride to prepare a magnesium fluoride coating layer on the magnesium alloy, and coating the fluoride coated layer with a biopolymer solution to form a biopolymer layer.

The method for preparing a dual-layer magnesium alloy with improved corrosion resistance according to the present invention includes polishing the surface of the magnesium alloy.

In the present invention, the magnesium alloy may be an alloy further including at least one metal selected from the group consisting of zinc, manganese, calcium, zirconium, yttrium, molybdenum, niobium, tantalum, titanium, strontium, chromium, silicon, phosphorus, nickel and iron.

A total weight of the metal, apart from magnesium, may be less than 10% by weight, with respect to the total weight of the alloy, but the present invention is not limited thereto.

In an embodiment of the present invention, a magnesium alloy substrate including zinc, zirconium and magnesium was used.

For effective surface coating, surface treatment of the magnesium alloy is important. In an embodiment of the present invention, for effective surface coating of magnesium alloys, the substrate was mechanically polished with silicon carbide paper up to 1,200 grit in order to secure uniform surface roughness of the substrate of the magnesium alloy. Samples were then degreased with acetone for 10 min, followed by rinsing with deionized water and dried using a warm stream of air.

The method for preparing a dual-layer coating on magnesium alloy with improved corrosion resistance according to the present invention includes treating the polished magnesium alloy with fluoride to prepare a magnesium fluoride coating layer on the magnesium alloy.

In the present invention, the fluoride may be hydrofluoric acid.

Surface coating is one reliable and efficient method to improve corrosion resistance. A wide range of surface coatings such as conversion coatings, inorganic coatings, polymer coatings and combined coatings have been applied to increase corrosion resistance. Among various anti-corrosion coating treatments, chemical conversion is one of the most simple, effective and economical processes.

In an embodiment of the present invention, chemical conversion treatment using hydrofluoric acid to form a magnesium fluoride ($MgF_2$) coating has been used to improve the corrosion resistance of potential degradable Mg-based implants with good compactness, low water solubility, and high adhesive strength. In addition, is easy to form a uniform coating on implants with a complex shape and harmless release of fluorine ions into the organism. For successful biomedical application of magnesium, an ideal coating should have improved corrosion resistance, good cell compatibility and acceptable degradation rate of magnesium to satisfy healing requirements.

According to the present invention, for fluoride treatment on Mg, prepared samples were immersed vertically in a plastic bottle containing 48 wt % hydrofluoric acid (HF, Sigma Aldrich, USA) at room temperature for 24 hours under constant stirring. The treated samples were then rinsed thoroughly with deionized water and air dried to prepare fluoride-coated magnesium alloys, which were referred to as $MgF_2$.

The method for preparing the dual-layer coating on magnesium alloy with improved corrosion resistance according to the present invention includes coating the inner fluoride layer with a biopolymer solution to form an outer biopolymer layer.

In the present invention, the biopolymer may include an organic material non-harmful to humans and be, for example, a biocompatible or biodegradable polymer. Non-limiting examples of the biopolymer may be selected from the group consisting of polyetherimide (PEI), polycaprolactone (PCL), chitosan, polylactic acid (PLA), polyglycolic acid (PGA), poly-ε-caprolactone-copolymers (PCLA), poly-ε-caprolactone-glycolic acid copolymers (PCGA), polylactic acid-glycolic acid copolymers (PLGA), polyethylene glycol (PEG), polydioxanone (PDO), polytrimethylene carbonate (PTMC), polyamino acid, polyanhydride, polyorthoester, polyphosphazene, polyiminocarbonate, polyphosphoester, polyhydroxyvalerate, copolymers thereof and mixtures thereof.

The biopolymer solution may be prepared by dissolving the biopolymer in dichloromethane.

In an embodiment of the present invention, in order to form a biopolymer layer on the fluoride-coated magnesium alloy, polycaprolactone (PCL, Mn: 70000-90000, Sigma-Aldrich, USA) was used and the biopolymer layer was dissolved in dichloromethane to prepare a polycaprolactone solution.

For formation of the polycaprolactone (PCL) coating layer, dip coating was used. Polycaprolactone (PCL) granules were dissolved in dichloromethane (DCM) as a solvent with magnetic stirring for 5 hours to prepare a polycaprolactone solution. Then, hydrofluoric acid (HF)-coated substrates were immersed in the prepared solution for 45 seconds to allow wetting of the substrate. In order to obtain a stain-free surface, samples were slowly mechanically pulled out of the solution at a speed of 1 mm/s. All coated samples were finally vacuum dried for 12 hours. All specimens were heated to 50° C. for 10 min to remove moisture and entrapped air from substrate surfaces before immersing in the prepared PCL solution to prepare a magnesium alloy provided with dual layer $MgF_2$/PCL coatings, which will be referred to as $MgF_2$/PCL herein below.

Polycaprolactone (PCL) is a promising semicrystalline aliphatic polymer widely used owing to good biocompatibility, significant toughness and outstanding mechanical properties thereof. PCL is a good candidate for bone tissue engineering because of its biocompatibility, bioresorbability, higher fracture energy and slow degradation rate. Moreover, PCL is hydrophobic, making it suitable for coating on magnesium to control high corrosion rate thereof.

In the present invention, the fluoride coating layer may have a thickness of 1.2 to 3.2 µm and the biopolymer layer may have a thickness of 2.3 to 4.3 µm.

When the thickness of the fluoride layer is less than 1.2 µm, the desired effect of improving corrosion resistance and/or the effect of improving the interfacial adhesion with the biopolymer layer cannot be obtained, and the thickness is limited to 3.2 µm with immersion time as longer immersion time in hydrofluoric acid showed no increase in thickness. Moreover, it is preferable to have a thin inner layer as the implants should not unnecessarily thick for the better adhesion of outer biopolymer coating layer.

When the biopolymer layer is formed to a thickness of less than 2.3 µm, the biopolymer layer cracks which may cause the inner magnesium-containing substrate to be easily exposed and rapidly corroded, and when the biopolymer layer is formed to a thickness higher than 4.3 µm, it is excessively thick, thus requiring a long time for the PCL based implants to be completely decomposed and absorbed.

Figure 2:
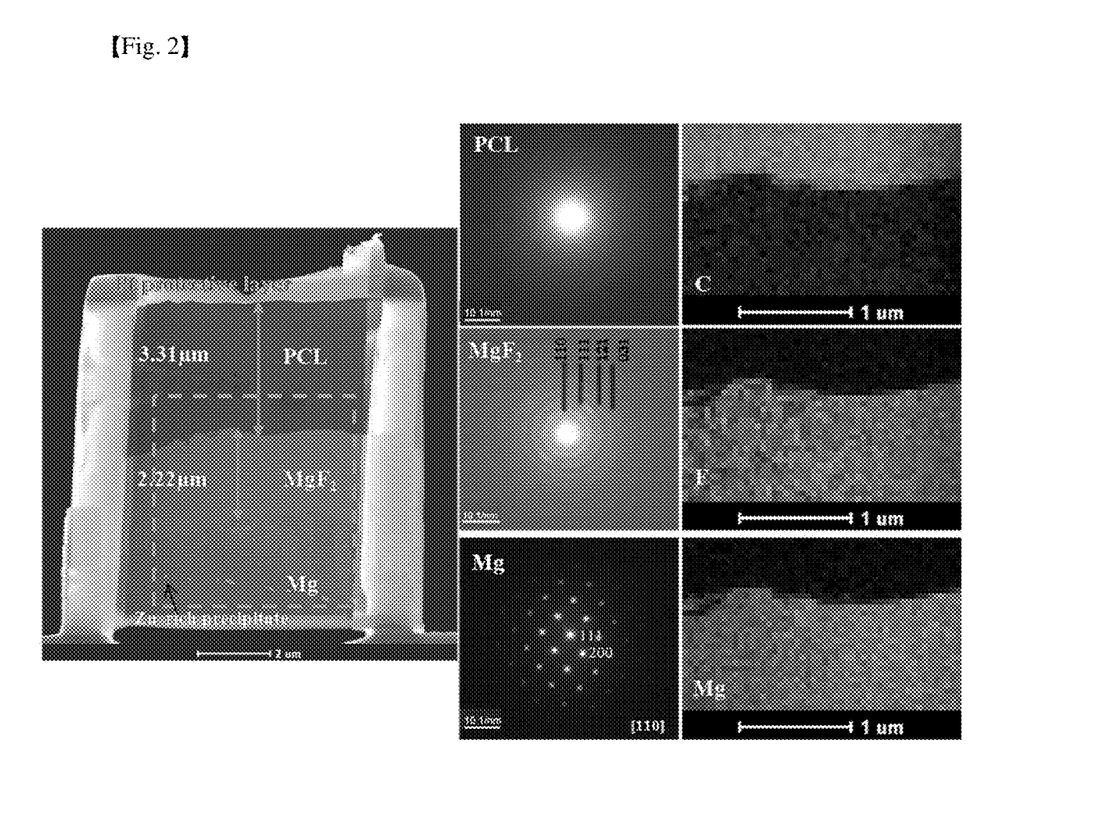
FIG. 2 shows a dark field TEM image showing the cross-section of dual $MgF_2$/PCL coatings along with the corresponding SAD pattern and mapping profile.

In an embodiment of the present invention, both the outer PCL and inner $MgF_2$ coatings are homogenously distributed throughout the substrate (FIG. 2).

In addition, in the $MgF_2$/PCL, the thickness of the $MgF_2$ film was approximately 2.2 µm and the thickness of outer PCL coating was approximately 3.3 µm (FIG. 2), regardless of surface irregularity.

In addition, in an embodiment of the present invention, analysis results of the surface roughness of $MgF_2$/PCL coating revealed that roughness was found to be 49.8 nm, which secures good biocompatibility. Contact angles of Mg alone (bare Mg), $MgF_2$ and $MgF_2$/PCL coatings were 118±3.2°, 111±2.7° and 92±1.8°, respectively. Dual layered coatings increased hydrophilicity due to decreased surface contact angle, compared to uncoated substrates, so that cell adhesion, diffusion and proliferation can be improved.

In addition, in an embodiment of the present invention, uncoated Mg alloy was seriously corroded, while $MgF_2$ and $MgF_2$/PCL coating samples effectively inhibited decomposition in a PBS solution, which indicates that dual-layer coating exhibits better corrosion resistance than bare Mg or fluoride-treated samples.

In addition, in an embodiment of the present invention, analysis results of biocompatibility of $MgF_2$, PCL and $MgF_2$/PCL coatings revealed that the $MgF_2$/PCL coating has low cytotoxicity, excellent cell proliferation and adhesion and thus superior biocompatibility.

In conclusion, as compared to fluorine coating alone or uncoated magnesium alloy, a magnesium alloy with a dual $MgF_2$/PCL coating exhibits excellent corrosion resistance and biocompatibility.

In another aspect of the present invention, provided is an implant for fixing bones including the dual-layer coated magnesium alloy with improved corrosion resistance prepared by the method.

As described above, the dual-layered magnesium alloy with improved corrosion resistance is useful as an implant for fixing bones. The dual-layered magnesium alloy has an appropriate strength, based on the magnesium alloy substrate as a metal and is thus advantageous for enduring load, and can improve corrosion resistance through fluoride and biopolymer coating to maintain the strength and shape for a predetermined period of time, and is thus suitable as an implant for fixing damaged bones upon injection in vivo.

In another aspect of the present invention, provided is a magnesium alloy with improved corrosion resistance including a magnesium alloy, a magnesium fluoride coating layer formed on the alloy, and a biopolymer layer coated onto the fluoride coating layer.

As described above, the magnesium alloy, the fluoride coating layer formed on the alloy, the biopolymer layer coating onto the fluoride coating layer and corrosion resistance have been described above.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Hereinafter, examples of the present invention will be described with reference to the annexed drawings in detail to such an extent that a person having ordinary knowledge in the art to which the present invention pertains can easily implement the examples. However, the present invention can be realized in various forms and is not limited to the examples described herein.

Example 1: Dual-Layer $MgF_2$/PCL Coating

The novel dual-layer $MgF_2$/PCL coating was developed on the surface of Mg (zk60) alloy using chemical conversion and dip coating respectively. These dual-layer coatings were prepared with the intent of reducing and controlling the initial corrosion rate and increasing biocompatibility.

1-1: Surface Preparation of Magnesium Alloy

Commercial ZK60 magnesium alloy substrates with dimensions of 10 mm×10 mm×2 mm were used in the present invention. The chemical composition (wt %) is zinc (Zn) 5.5, zirconium (Zr) 0.49 and the remainder of magnesium (Mg). Surface preparation of the Mg alloy is crucial for effective surface coating. In this regard, prior to the coating deposition, substrates were first mechanically polished with silicon carbide papers up to 1200 grit to ensure the same surface roughness. Samples were then degreased with acetone for 10 min, followed by rinsing with deionized water and dried in a warm stream of air.

1-2: Formation of Fluoride Coating Layer

For fluoride treatment of Mg, prepared samples were immersed vertically in a plastic bottle containing 48 wt % hydrofluoric acid (HF, Sigma Aldrich, USA) at room temperature for 24 hours under constant stirring. Treated samples were then rinsed thoroughly with deionized water and air dried. The fluoride-treated coatings were referred to as $MgF_2$ below.

1-3: Formation of Biopolymer Layer

For dual layer PCL coating on Mg, polycaprolactone (PCL, Mn: 70000-90000, Sigma-Aldrich, USA) and dichloromethane (DCM, Sigma-Aldrich, USA) were used as starting reagents for deposition of polymer coating on the initial fluoride treated layer. A simple dip-coating technique was employed for PCL layer deposition. Briefly, PCL granules were dissolved in DCM as a solvent with magnetic stirring for 5 hours. HF-coated substrates were then immersed in the prepared solution for 45 seconds to allow wetting of the substrate. In order to obtain a stain-free surface, specimens were slowly and mechanically pulled out of the solution at a speed of 1 mm/s. All coated samples were finally vacuum dried for 12 hours. All specimens were heated to 50° C. for 10 min to remove moisture and entrapped air from substrate surfaces before immersing in the prepared PCL solution. The dual layered coatings were labeled as $MgF_2$/PCL coatings in the below sections.

The physical characterizations such as SEM, TEM, XRD, XPS, EDS, AFM, and contact angle were initially carried out for dual $MgF_2$/PCL coatings to understand the surface morphology, phase structure, chemical composition, roughness, and wettability of the system. Later, performance in terms of adhesive strength, hardness, in vitro degradation (pH, hydrogen evolution, degradation rate) and in vitro biocompability (cell viability, cell adhesion and cell proliferation using MC3T3-E1 cells) were conducted and compared with a single layered $MgF_2$ coating and an uncoated Mg alloy.

Figure 1:
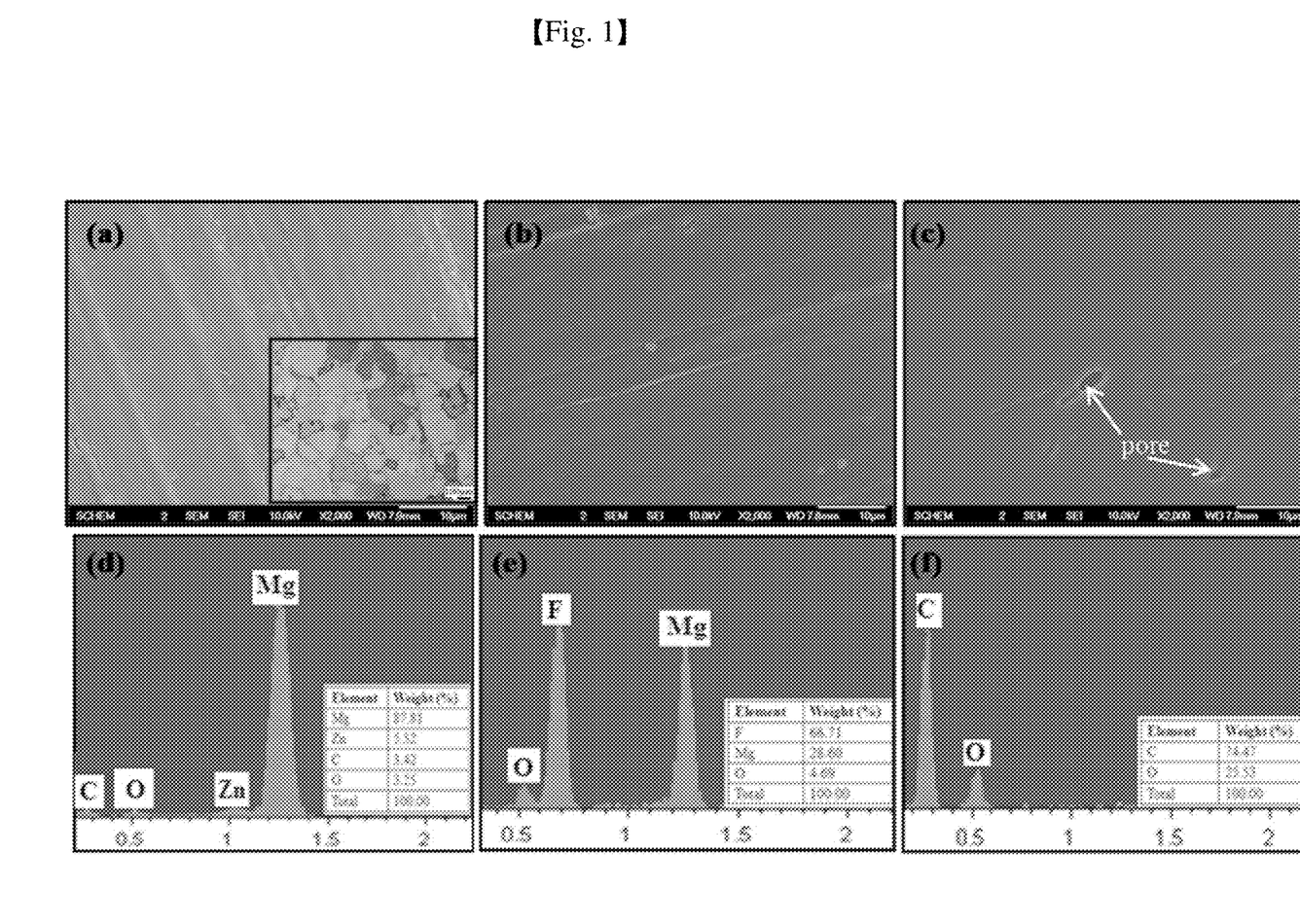
FIG. 1 shows SEM images of (a) as-received Mg alloy with optical micrograph (inset), (b) $MgF_2$, and (c) dual $MgF_2$/PCL coatings along with EDX (d-f)

Test Example 1: Analysis of Morphological Properties and Elemental Compositions of Mg Alloy, Surface-Modified $MgF_2$ and Dual-Layer $MgF_2$/PCL Coatings Morphological features and elemental compositions of the as-received Mg alloy, surface-modified $MgF_2$, and dual $MgF_2$/PCL coatings are shown in FIG. 1. The optical image of the bare Mg alloy reveals coarser and equiaxed grains of nearly 100-200 µm. It is also observed that some eutectics and precipitates of intermetallic MgZn phases were present within grains as well as along the grain boundaries (black spots) (FIG. 1A, inset). The surface of the polished Mg alloy appeared to be slightly coarse with abrasive vertical lines as shown in the SEM image (FIG. 1A). After immersion in an HF solution for 24 hours, the initial metallic grey color of Mg alloy (FIG. 1A) was uniformly changed to dark black (FIG. 1b). A fluoride-coated surface appeared to be completely covered by a compact and uniform film with few abrasive scratches occurring due to mechanical polishing. A transparent porous film was found throughout the fluoride-treated surface after PCL treatment (FIG. 1C). The developed dual $MgF_2$/PCL coating was found to be uniform and crack-free (FIG. 1C). Such morphological modification was supported by transformation of the chemical composition of Mg, $MgF_2$, and $MgF_2$/PCL coatings. EDX analysis showed that magnesium (Mg) and zinc (Zn) elements were present in the Mg alloy with minute impurities of carbon (C) and oxygen (O) (FIG. 1D). Quantitative analysis results were profoundly alternated after fluoride treatment and PCL coating. The presence of fluorine (F) apart from Mg and O confirmed formation of the $MgF_2$ film on the substrate. Small traces of oxygen in the film might be attributed to hydroxides of $Mg(OH)_2$ (FIG. 1E). The presence of C and O elements in $MgF_2$/PCL coatings indicated successful coating of PCL onto the fluoride-coated surface (FIG. 1F).

Figure 3:
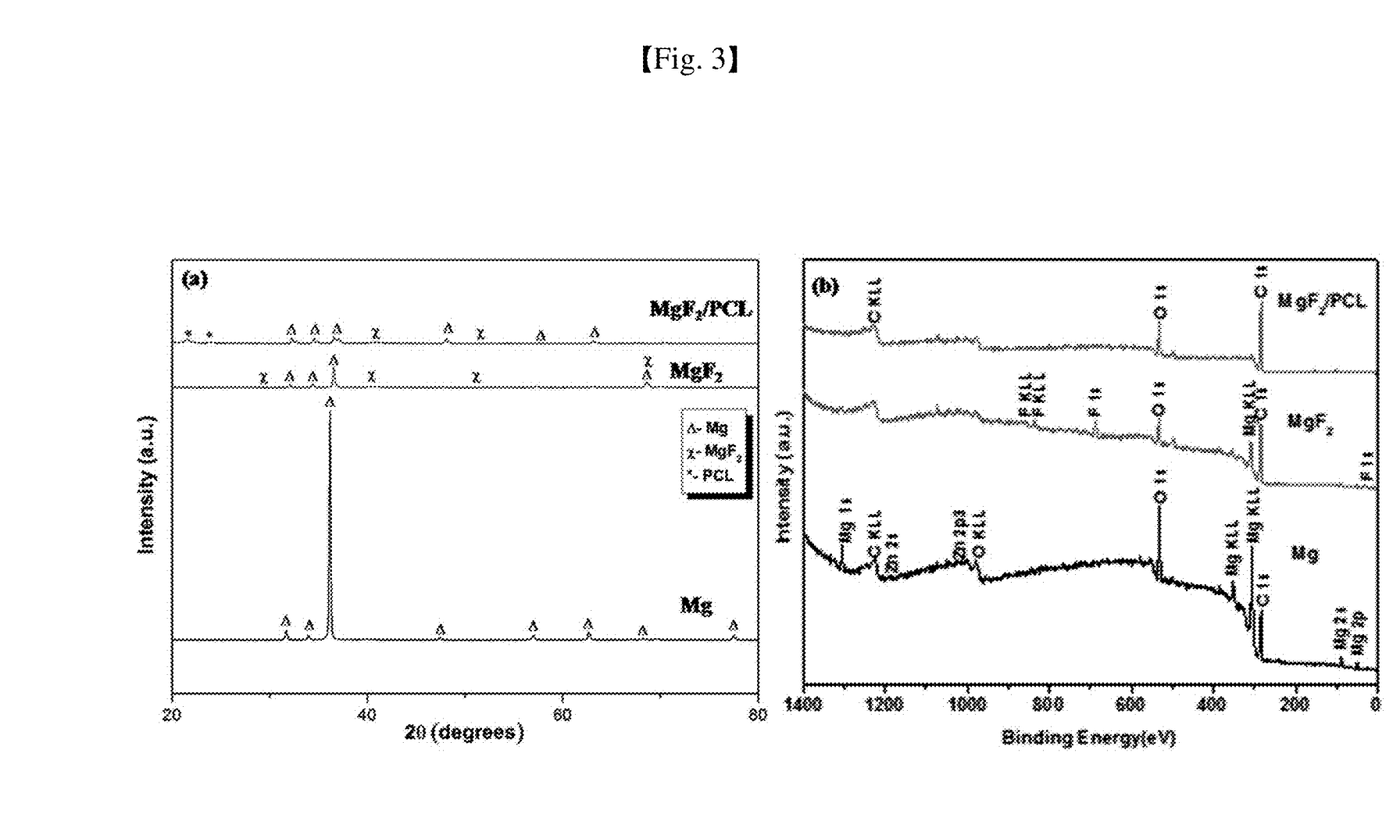
FIG. 3 shows results of (a) XRD and (b) XPS analysis of a Mg alloy, $MgF_2$ and $MgF_2$/PCL coatings.

Test Example 2: Analysis of SAD Patterns and Mapping Profiles of Dual-Layer $MgF_2$/PCL Coatings Cross-sectional morphology of dual-layer $MgF_2$/PCL coating was investigated by TEM along with selected area electron diffraction (SAD) patterns and mapping profile. Results are shown in FIG. 2. High angle annular dark field (HAADF) images showed clear interfaces of outer PCL, intermediate $MgF_2$ and Mg substrate. The thickness of the compact $MgF_2$ film was approximately 2.2 μm and that of the outer PCL coating was around 3.3 μm (FIG. 2), regardless of surface irregularity. No defects or cracks were observed at the interface of both coatings, showing evidence of good adhesion between the outer layer and the inner layer as well as between the inner layer and the Mg substrate. SAD patterns were obtained from each layer to confirm crystal structures. As expected, the SAD pattern of the Mg alloy showed a hexagonal structure. However, in the fluoride treated layer, the $MgF_2$ film had a tetragonal nanocrystalline structure (space group: P42-nm). The amorphous nature of the PCL coating contributed to the diffused ring observed in the SAD pattern (FIG. 2). These results corresponded to results of XRD studies (FIG. 3A). The mapping profile displayed that C was mainly distributed at the outer layer, whereas F became the main element in the inner layer besides Mg, confirming that the dual coating was formed on the Mg substrate. Compositional analysis further confirmed homogenous distribution of both outer PCL and inner $MgF_2$ coatings throughout the substrate (FIG. 2).

Test Example 3: XRD and XPS Analysis of Mg Alloy, $MgF_2$ and $MgF_2$/PCL Coatings FIG. 3 shows results of (a) XRD and (b) XPS analysis of Mg alloy, $MgF_2$ and $MgF_2$/PCL coatings.

XRD and XPS spectra of Mg alloy, $MgF_2$, and $MgF_2$/PCL coatings are shown in FIG. 3. X-ray diffraction pattern of the Mg alloy showed a Mg phase with a hexagonal system (ICDD No: 01-071-6543), as shown in FIG. 3A. After fluoride treatment for 24 hours, $MgF_2$ (ICDD No: 01-070-8288) peaks with a tetragonal structure was primarily found along with Mg. However, the intensity of the $MgF_2$ peak was quite low compared to that of Mg, suggesting that the fluoride coating layer was thin. Mg can react with HF to yield $MgF_2$ by displacement reaction and insoluble $MgF_2$ can form a barrier coating on Mg. Broad amorphous peaks of PCL were observed at 21° C. and 24° C. (ICDD No: 00-034-1796) apart from peaks of Mg and $MgF_2$ in $MgF_2$/PCL coatings (FIG. 3A).

In order to fully understand the coating composition, chemical compositions of elements at the surface of Mg, $MgF_2$, and $MgF_2$/PCL coatings were investigated by XPS (FIG. 3B). The chemical composition of Mg alloy consisted of Mg and Zn with high concentrations of C and O. Carbon in XPS surface scan is commonly attributed to environmental impurities due to extraneous hydrocarbons. An oxygen rich layer might have originated from hydrocarbons or due to formation of MgO and $Mg(OH)_2$ upon exposure to air. After pretreatment with HF, an additional peak of fluorine in XPS spectra was observed, signifying the deposition of a $MgF_2$ film on the substrate. Moreover, binding energy of F1s on the fluoride-coated surface was around 685 eV, which was correctly matched to $MgF_2$ value, i.e. 685 eV, with reference to a standard database. Also, the binding energy of O1s at around 533 eV could be ascribed to presence of small amounts of $Mg(OH)_2$ which is also evident in EDX (FIG. 1E). After PCL modification, an increase in C1s and O1s without characteristic peaks associated with Mg and F confirmed complete coverage of the PCL coating on the $MgF_2$ film. XPS results correspond to conclusions obtained from EDX data (FIGS. 1D to 1F). Both XRD and XPS studies verified that PCL was successfully anchored on the HF treated surface.

Figure 4:
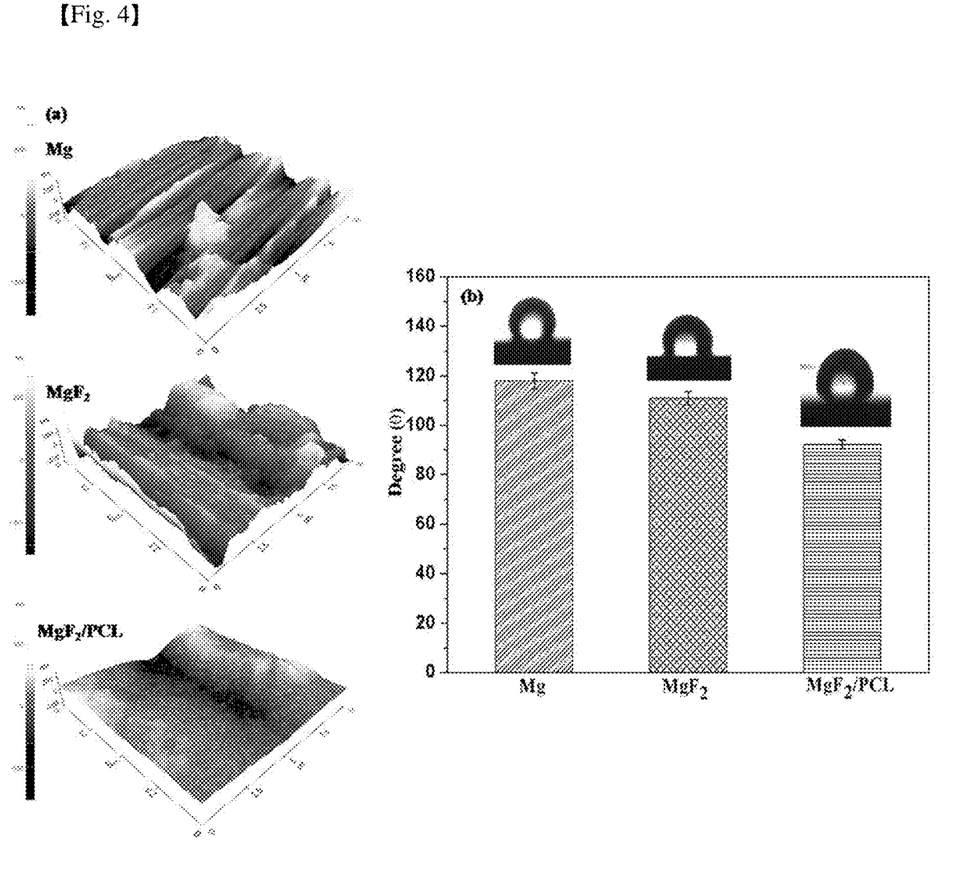
FIG. 4 shows (a) AFM and (b) wettability studies of a Mg alloy, $MgF_2$ and $MgF_2$/PCL coatings.

Test Example 4: Roughness and Wettability Analysis of Mg Alloy, $MgF_2$ and $MgF_2$/PCL Coatings Three-dimensional AFM images of Mg alloy, $MgF_2$ and $MgF_2$/PCL coatings are shown in FIG. 4A. The average roughness value (Ra) of the untreated Mg alloy was found to be 40.7 nm. All of the coated surfaces were found to be relatively rougher than uncoated Mg alloy. The roughness value after fluoride ($MgF_2$) coating was significantly increased to 66.3 nm. Minute pores generated on the surface due to acid immersion might be ascribed to the above increment. The surface morphology was described by the precipitation of intermetallic particles (MgZn) on the surface and at grain boundaries (FIG. 1A). Hydrogen released at cathodic sites could facilitate the emergence of pores in the resulting film. The dual-layer PCL coated surface was smoother than the $MgF_2$ film and the average roughness value was found to be 49.8 nm. Surface roughness also has a huge impact on corrosion resistance of samples. Reduction in surface roughness can lead to decreased surface area for corrosive attack. Also, surface roughness is a pivotal factor influencing biocompatibility. It has been reported that coatings with surface roughness in an optimum range of 20-100 nm can promote cell adhesion and longevity.

Photographs of water droplets on the surface of uncoated Mg and coated $MgF_2$ and $MgF_2$/PCL samples and variation in wettability thereof are shown in FIG. 4B. Contact angles of bare Mg, $MgF_2$, and $MgF_2$/PCL coatings were 118±3.2°, 111±2.7°, and 92±1.8°, respectively. These results indicated that both coatings increased the surface hydrophilicity compared to uncoated substrates. An increase in hydrophilicity could enhance adhesive interaction between water droplets and the surface, thus decreasing contact angle. The lower contact angle can strongly support cell adhesion, spreading and proliferation.

Test Example 5: Evaluation of Scratch Adhesion Strength of $MgF_2$, PCL and $MgF_2$/PCL Coatings and Hardness Studies of Mg Alloy and Dual $MgF_2$/PCL Coatings FIG. 5 shows evaluation of (a) scratch adhesion strength of $MgF_2$, PCL and $MgF_2$/PCL coatings, and (b) hardness studies of Mg alloy and prepared dual-layer $MgF_2$/PCL coatings.

The bonding strength between the coating and substrate plays a crucial role in determining reliability as well as performance of the coated substrate as an effective implant material. Scratch adhesion testing was performed to evaluate adhesion strength of $MgF_2$ and $MgF_2$/PCL coatings on Mg alloy (FIG. 5A). For comparison, adhesion strength of plane PCL coating on Mg alloy was also investigated (FIG. 5A). Adhesion strength values of single layered $MgF_2$, PCL and dual $MgF_2$/PCL coatings were found to be 65.39±2.2 mN, 42.5±1.2 mN and 58.68±3.27 mN, respectively. These results indicated that both $MgF_2$ film and $MgF_2$/PCL coatings were strongly adhered to the substrate, compared to PCL coated substrates. It was clearly seen that the adhesion strength between PCL and the substrate could be improved through interlayer $MgF_2$ coating. The relatively increased adhesion of $MgF_2$/PCL coatings over PCL coatings was more likely due to the mechanical interlocking as PCL solution was infused into the $MgF_2$ film sealing the micropores and thus forms a stronger bonding layer with the $MgF_2$ film. In addition, the higher interfacial adhesion strength of the $MgF_2$ film with the PCL might be due to the formation of hydrogen bonds between —OH groups present in the fluoride treated surface and the =O group of PCL. The chemical composition of the $MgF_2$ film showed the existence of O along with F elements as evident from EDX (FIG. 1E) and XPS (FIG. 3B) analysis which might contribute to $OH^-$ ions on its surface.

Figure 5:
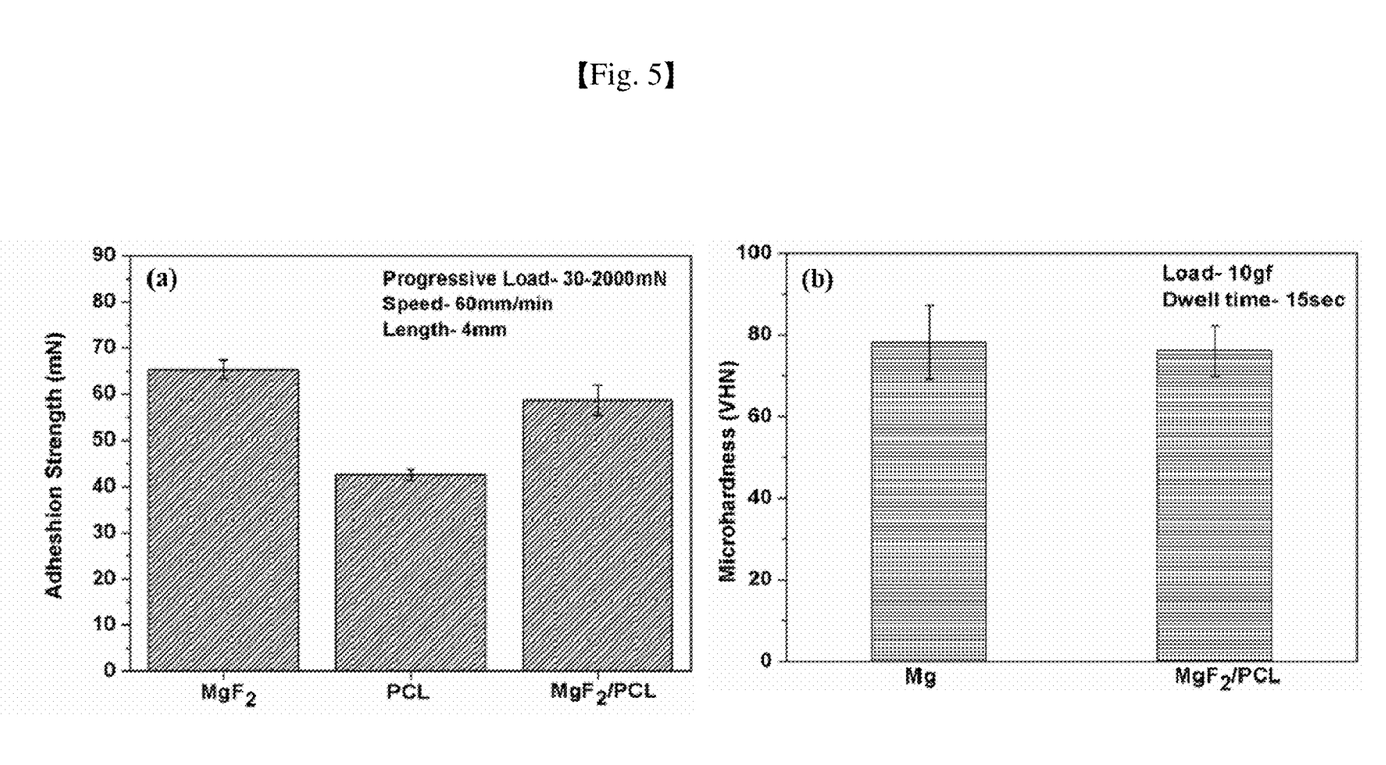
FIG. 5 shows evaluation of (a) scratch adhesion strength of $MgF_2$, PCL and $MgF_2$/PCL coatings, and (b) hardness studies of Mg alloy and prepared dual $MgF_2$/PCL coatings.

Vickers microhardness values of uncoated sample and dual $MgF_2$/PCL coating are shown in FIG. 5B. ZK60 Mg alloy has an average micro-hardness of 78±9 VHN. The $MgF_2$/PCL dual-layer coating has a hardness of 76±6.3 VHN. The uncoated sample and dual-coated sample have no great variation in hardness. This means that the $MgF_2$/PCL dual-layer coating can endure high load and impart better corrosion to the Mg substrate.

Figure 6:
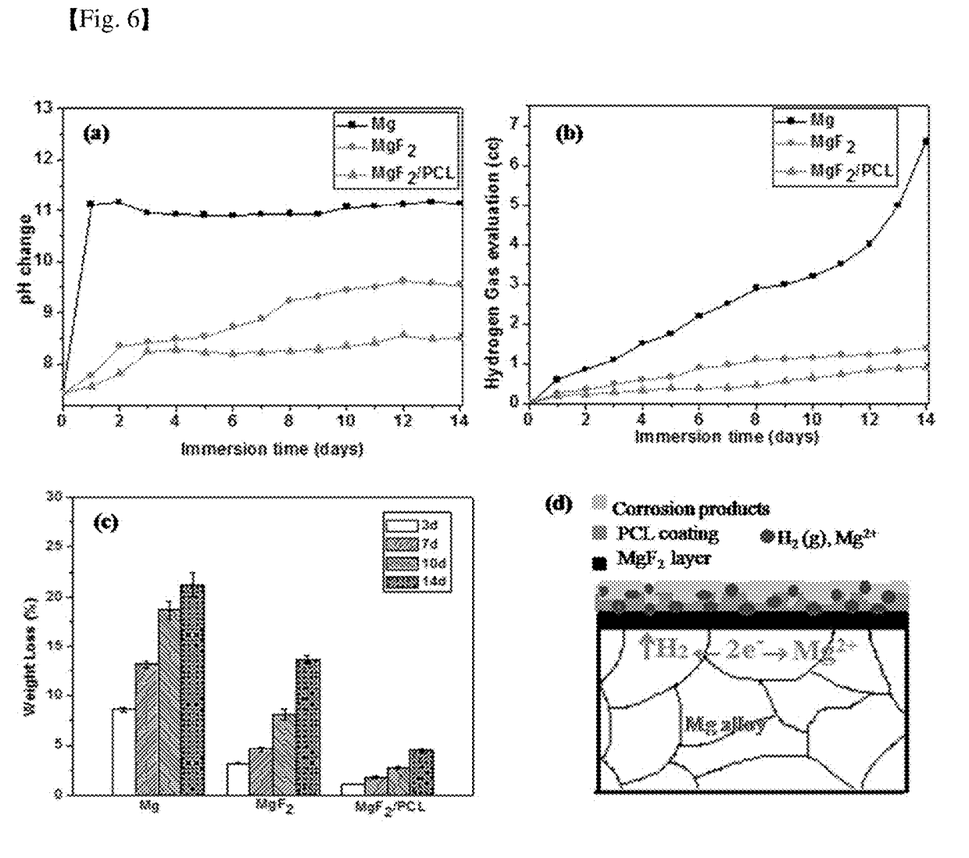
FIG. 6 shows (a) pH change, (b) hydrogen released volume and (c) weight loss as a function of immersion time in PBS solution over a period of 14 days of Mg alloy, $MgF_2$ and $MgF_2$/PCL coating, and (d) a schematic diagram of corrosive attack in the $MgF_2$/PCL coating on Mg alloy in PBS solution.
Figure 7:
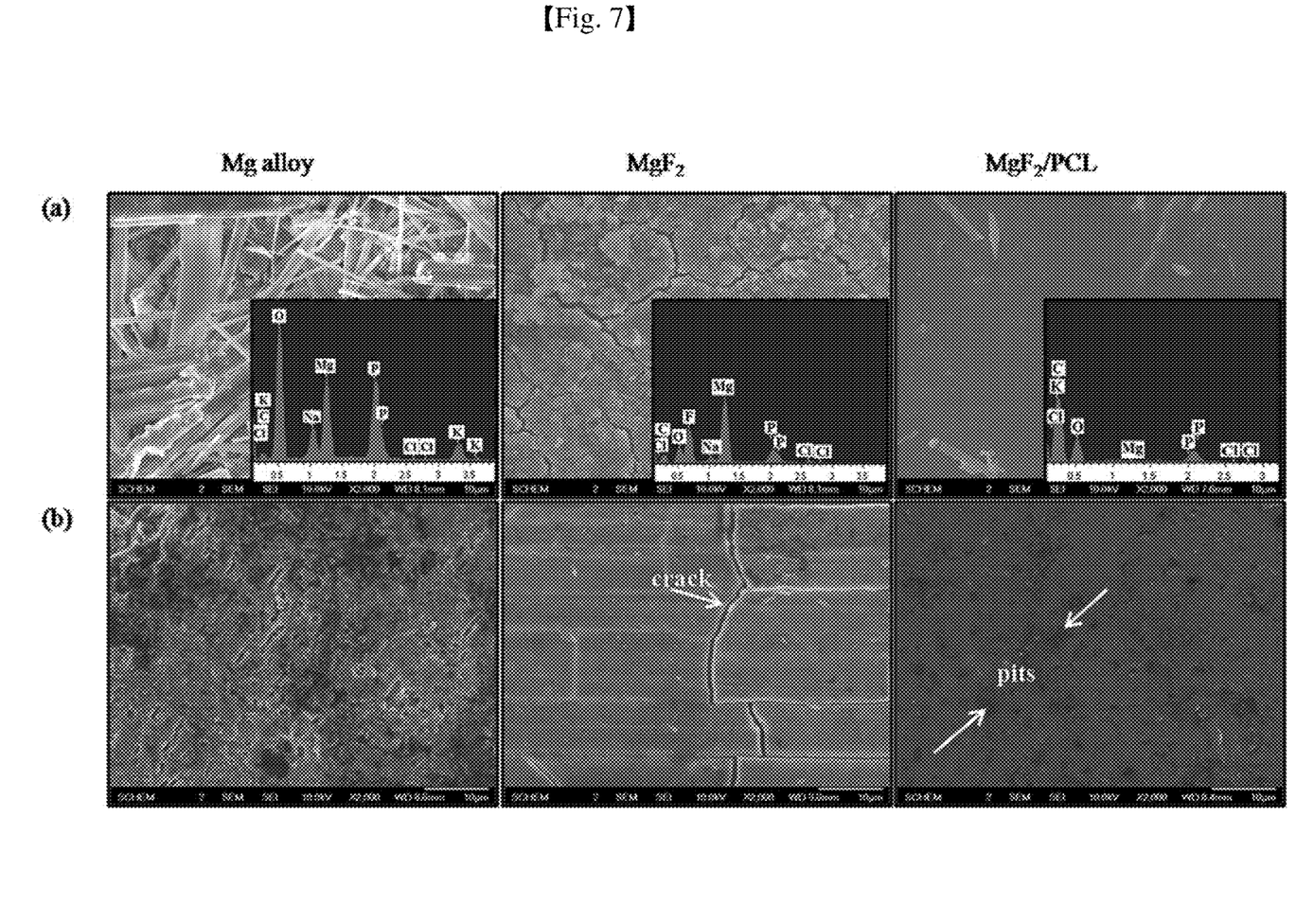
FIG. 7 shows SEM images of Mg alloy, $MgF_2$ and $MgF_2$/PCL coatings (a) after immersion in PBS solution for 14 days along with EDS and (b) after washing of corroded products.

Test Example 6: Corrosion Resistance Analysis of Mg, $MgF_2$ and $MgF_2$/PCL Coatings The primary goal of surface modification is to delay initial degradation rate or enhance corrosion resistance of biodegradable magnesium. FIG. 6 shows (a) pH change, (b) hydrogen gas evolution, (c) weight loss as a function of immersion time for Mg alloy, $MgF_2$ and $MgF_2$/PCL coatings after immersion in PBS solution for 14 days, and (d) a schematic diagram showing corrosive attack in the $MgF_2$/PCL coating on Mg alloy in PBS solution.

pH change, hydrogen evolution and variations in weight loss for Mg alloy, $MgF_2$ and $MgF_2$/PCL coatings after immersion in PBS solution at 37° C. for 14 days are shown in FIG. 6A. Variation in pH as a function of time for different samples immersed in PBS solution is shown in FIG. 6A. The pH value of dual $MgF_2$/PCL coatings was initially increased for 2 days followed by relatively stable behavior afterwards. In contrast, the pH value of Mg alloy was first increased intensely within 1 day and then showed an almost constant behavior (FIG. 6A). After 14 days of incubation, the pH values of Mg, $MgF_2$ and $MgF_2$/PCL were 11.07, 9.45, and 8.35, respectively. The pH values for both $MgF_2$ and $MgF_2$/PCL were found to be lower than that of bare Mg alloy. This suggested that the protective outer layer of PCL and the relatively compact inner layer of $MgF_2$ effectively controlled degradation of the magnesium substrate. The less significant increase in pH values of $MgF_2$/PCL coated substrates could be attributed to the release of alkaline ions. It is apparent that the presence of an inner layer of $MgF_2$ eases local alkalization and lessens acidification of the medium as the polymer (PCL) degrades into acids. However, the pH values of the samples after a long incubation time (after 2 days) were mainly dependent on degradation of the Mg substrate. The increase in pH of $MgF_2$ could be due to more rigorous destruction of the $MgF_2$ coating than that of the dual $MgF_2$/PCL coating. Hence, the Mg substrate with the $MgF_2$ coating was more degraded compared to the $MgF_2$/PCL coating at later stage. Reduction in the long-term protective ability of the $MgF_2$ coating might be due to the existence of micro-cracks in the coating evident in the SEM micrographs shown in FIG. 7B. These results indicated that the prominent alkalization effect on bare Mg alloy was effectively reduced by surface coatings. In other words, dual $MgF_2$/PCL coating could effectively prevent the penetration of immersion fluids (FIG. 6A).

Hydrogen gas evolution plots for the Mg, $MgF_2$ and $MgF_2$/PCL coated samples in the PBS solution for 14 days are shown in FIG. 6B. Results showed that the volume of released hydrogen was significantly reduced in $MgF_2$ and $MgF_2$/PCL coated samples compared to that in bare Mg alloy during the immersion period. The result was similar to the pH change behavior (FIG. 6A). Dual $MgF_2$/PCL coatings exhibited the lowest amount of hydrogen evolution (FIG. 6B). It was revealed that the uncoated Mg alloy had undergone severe corrosion whereas coated $MgF_2$ and $MgF_2$/PCL samples could efficiently inhibit degradation in the PBS solution. These results suggest that dual-layered coatings can offer higher corrosion resistance compared to bare Mg or fluoride-treated samples.

FIG. 6C shows the average weight loss of bare Mg, coated $MgF_2$ and $MgF_2$/PCL coating in PBS solution for time periods of 3, 7, 10, and 14 days incubated at 37° C. It was observed that $MgF_2$ coated samples displayed effectively lower weight loss rate compared to the Mg substrate. The rate of weight loss, as expected, further declined due to protection of the dual layer ($MgF_2$/PCL) on the Mg alloy which retards corrosion. Uncoated Mg alloy exhibited the highest weight loss rate among all samples. An increasing trend in rate of weight loss was noticed for all the samples with increase in exposure time. The percent weight losses of coated $MgF_2$ and $MgF_2$/PCL samples were about 13.6% and 4.5%, respectively, compared to Mg alloy (21.2%) after 14 days of immersion. The continuous increment in weight loss of coated samples with prolonged exposure time indicated delamination of the coating layers on the Mg substrate. This means that both $MgF_2$ and $MgF_2$/PCL coatings were not providing adequate protection for long-term immersion. In addition, it was found that the corrosion rate was more accelerated in the initial 3 days of exposure compared to prolonged immersion time (14 days) for uncoated Mg alloy (FIG. 6C). This could be explained by the fact that initially larger surface area was exposed to solution which in turn promoted exothermic reactions and thus increased corrosion rate. The higher concentration of chlorine and other salts might also contribute to the increased corrosion rate in the first few days. On the other hand, the corrosion rate of both $MgF_2$ and $MgF_2$/PCL coated samples notably increased with exposure time due to the detachment or weak adhesion of the protective layers after longer immersion in the PBS solution. Immersion tests revealed that dual $MgF_2$/PCL coated alloy experienced lesser corrosion attack compared with single layered $MgF_2$ coating and uncoated alloy samples.

FIG. 6D is a schematic diagram showing degradation mechanism of a dual $MgF_2$/PCL coated alloy after immersion in PBS solution. When dual coated samples were immersed in PBS, PBS penetrated from the porous structure of the PCL coatings to the Mg alloy substrate via the $MgF_2$ layer. As the corrosive PBS medium reached the Mg substrate early, immediate galvanic reactions between primary Mg and the secondary phases took place.

Test Example 7: SEM Images of Corroded Surfaces of Mg, $MgF_2$ and $MgF_2$/PCL Coatings FIG. 7 shows SEM images of a Mg alloy, $MgF_2$ and $MgF_2$/PCL coatings (a) after immersion in a PBS solution for 14 days along with EDS and (b) after washing of corroded products.

As per the electrochemical reactions, Mg metal from the substrate was converted into an insoluble magnesium hydroxide $Mg(OH)_2$ film with evolution of hydrogen gas ($H_2$). Hence, $Mg(OH)_2$ starts assembling at the alloy-coating interface and resulted in pH increase of the solution. Also, the evolved $H_2$ gas pushed away the coated PCL film which in turn weakened adhesion between the PCL coating and Mg alloy. Apart from film loosening, gas accumulation below the coating leads to crack formation and other coating failures. At the same time, aggressive salts such as chloride ions present in solution might damage the protective PCL layer by converting $Mg(OH)_2$ into soluble $MgCl_2$. Hence, the PCL film on the surface is readily dissolved leading to the generation of pits. Nucleation of pits on the surface of $MgF_2$/PCL coatings after immersion in PBS for 14 days is evident in SEM images (FIG. 7B). Also, depletion of the $Mg(OH)_2$ layer and utilization of $OH^-$ ions by the corrosion products released in PBS solution further accelerate solution penetration into the Mg alloy resulting in increase in corrosion rate.

SEM images of surfaces of Mg alloy, $MgF_2$, and $MgF_2$/PCL coating after immersion in PBS solution for 14 days along with EDX are shown in FIG. 7A. It can be clearly seen that bare Mg alloy was fully covered with corrosion products. On the other hand, fluoride-treated sample, $MgF_2$, showed network-like cracks with small precipitates evenly distributed over the entire surface of the alloy. The thicker corroded layer might be ascribed to the presence of micro-cracks in the coating caused by shrinkage of surface corrosion products during drying. However, a few white precipitates were observed on the dual $MgF_2$/PCL coated surface. EDX analysis of corroded surface compositions for different samples showed the presence of O, C, Na, K, Cl, and P. The existence of these elements suggests formation of $MgCl_2$, $Mg(OH)_2$ and other Na and K rich compounds in the corrosion product. Therefore, contents of these elements on the surface after immersion can be used to estimate the degree of corrosion occurring in each sample. It was observed that bare Mg alloy had many more corrosion products on the surface thereof than $MgF_2$ or $MgF_2$/PCL coated samples. Dual coated surfaces showed significantly lower concentrations of P and O with the absence of K or Na compared to bare Mg alloy. The lower concentration of Mg and higher concentration of C in $MgF_2$/PCL coated samples indicated that PCL coatings were still present after 14 days of immersion. However, in the case of $MgF_2$, traces of Na and P with relatively higher concentration of Mg resulted in destruction of fluoride coating on Mg substrate (FIG. 7B). SEM images of washed corroded surfaces are shown in FIG. 7B. Bare Mg surface showed a large number of cracks, dips and pits with severe degradation on the surface (A region). The crack formation caused surface shrinkage and dehydration of the corrosion products. The fluoride-treated surface showed slightly severer corrosion due to the presence of micro-cracks compared to $MgF_2$/PCL coated samples after 14 days of immersion. The cracks in $MgF_2$ coating can provide a suitable path for penetration of PBS solution into the coating (FIG. 7B). Hence, corrosion expands under the coating along with corrosion products that might result in weak adhesion of the coating and eventually lead to coating failure. Dual-layered coatings showed small pits on PCL surfaces (FIG. 7B). All corrosion surface images were consistent with degradation results during the whole immersion period of 14 days. It is well known that $MgF_2$ is more stable than MgO and $Mg(OH)_2$ and is efficient in resisting corrosive attack. Hence, in dual $MgF_2$/PCL coating systems, the outer PCL layer retards corrosive attack while the inner $MgF_2$ layer protects the Mg substrate from the aggressive medium when it crosses from the outer PCL layer. These results suggested that dual $MgF_2$/PCL-coated samples exhibit higher corrosion resistance than $MgF_2$ coating or Mg alloy.

Test Example 8: Biocompatibility Analysis of $MgF_2$ and $MgF_2$/PCL Coatings

Figure 8:
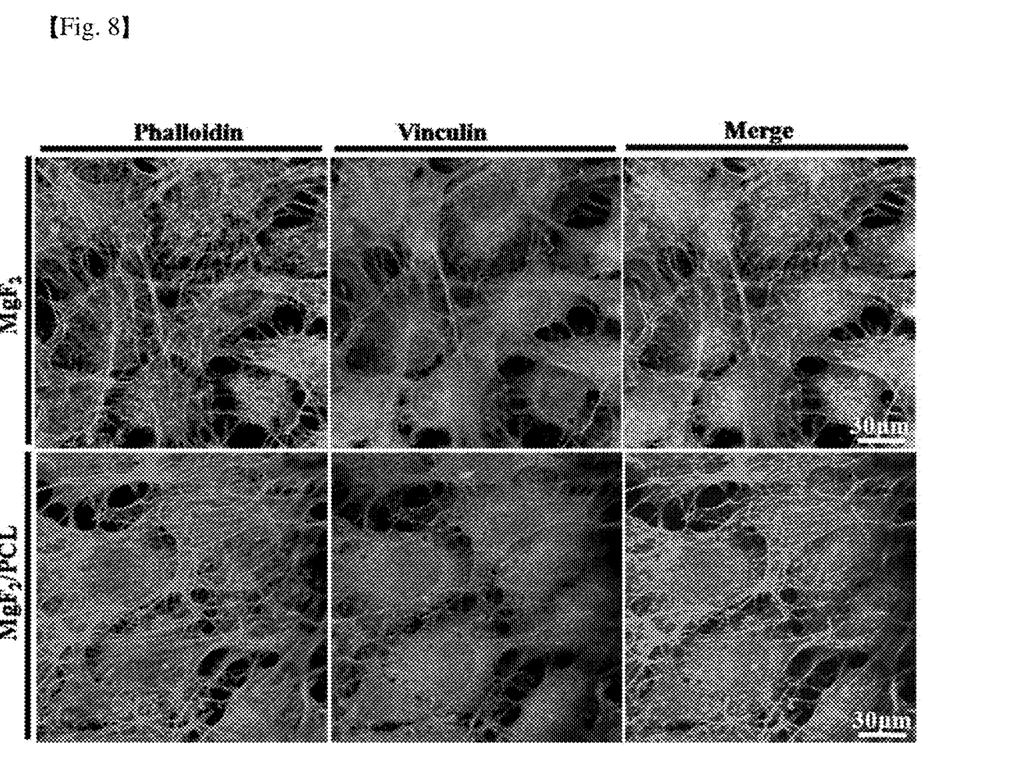
FIG. 8 shows confocal images of adhesion and attachment of MC3T3-E1 cells after seeding for 4 hours on $MgF_2$ and $MgF_2$/PCL coatings.

FIG. 8 shows confocal images of adhesion and attachment of MC3T3-E1 cells after seeding for 4 hours on $MgF_2$ and $MgF_2$/PCL coatings.

The degree of proliferation and adhesion of host cells on the substrate correlates with biocompatibility. Cell adhesion behavior of MC3T3-E1 cells on $MgF_2$ and $MgF_2$/PCL coatings after 4 h incubation is shown in FIG. 8. It was observed that cells were well attached to the surfaces of both coatings. Furthermore, staining for focal adhesion and the actin cytoskeleton were carried out. Phalloidin, Vinculin and nuclei were detected as green, red and blue respectively. The strongly developed cytoskeletal structure and interconnected cellular network were noticed for both coatings. However, it was clearly seen that $MgF_2$/PCL coatings exhibited higher cell attachment and more spreading than $MgF_2$ coating.

Figure 9:
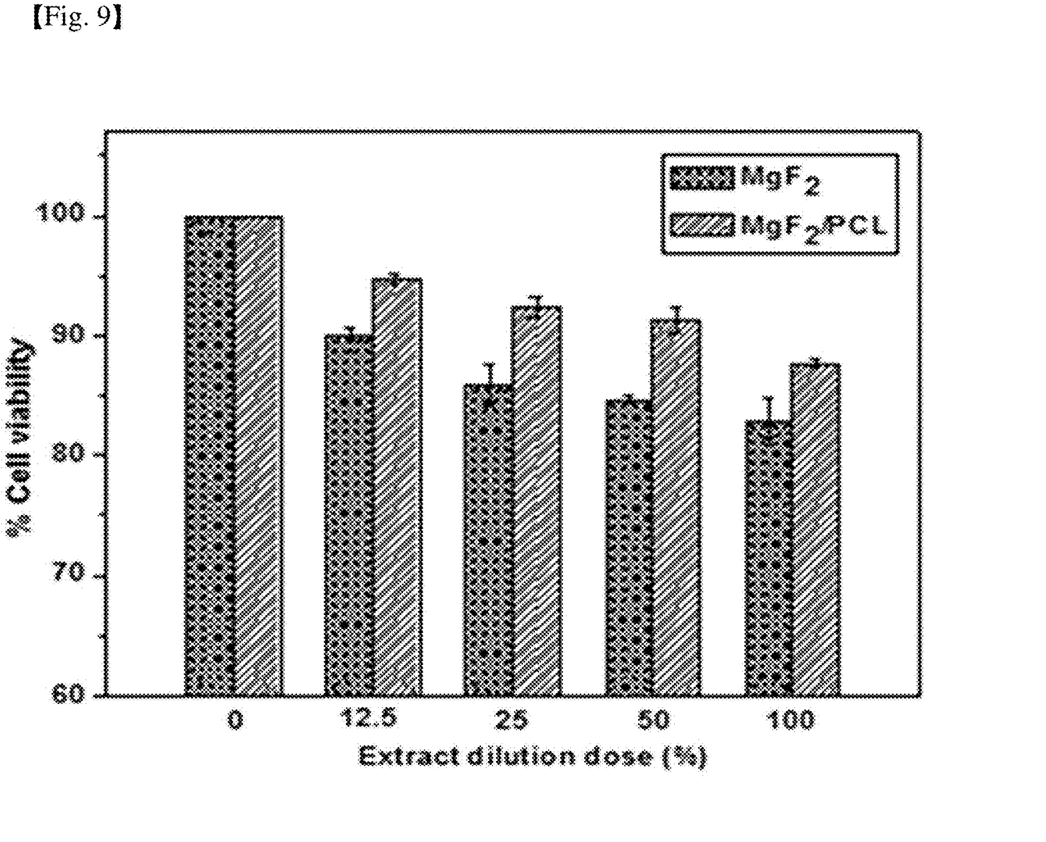
FIG. 9 shows cytotoxicity of $MgF_2$ and dual $MgF_2$/PCL against MC3T3-E1 cells. MTT assay was performed using indirect assay after 1 day incubation with increasing extract concentrations.

FIG. 9 shows analysis results of cytotoxicity of $MgF_2$ and dual $MgF_2$/PCL against MC3T3-E1 cells. MTT assay was performed using indirect assay after 1 day incubation with increasing extract concentrations.

Results of cell viability studies of $MgF_2$ and $MgF_2$/PCL coatings using indirect cell assay with increasing extract concentrations after 1 day of incubation are shown in FIG. 9. When the extract concentration was increased from 12.5% to 100%, the percent of cell viability was decreased from 90% to 82% for $MgF_2$ and from 95% to 87% for $MgF_2$/PCL coatings. $MgF_2$/PCL coatings showed higher cell viability than $MgF_2$ coatings at all extract concentrations.

Figure 10:
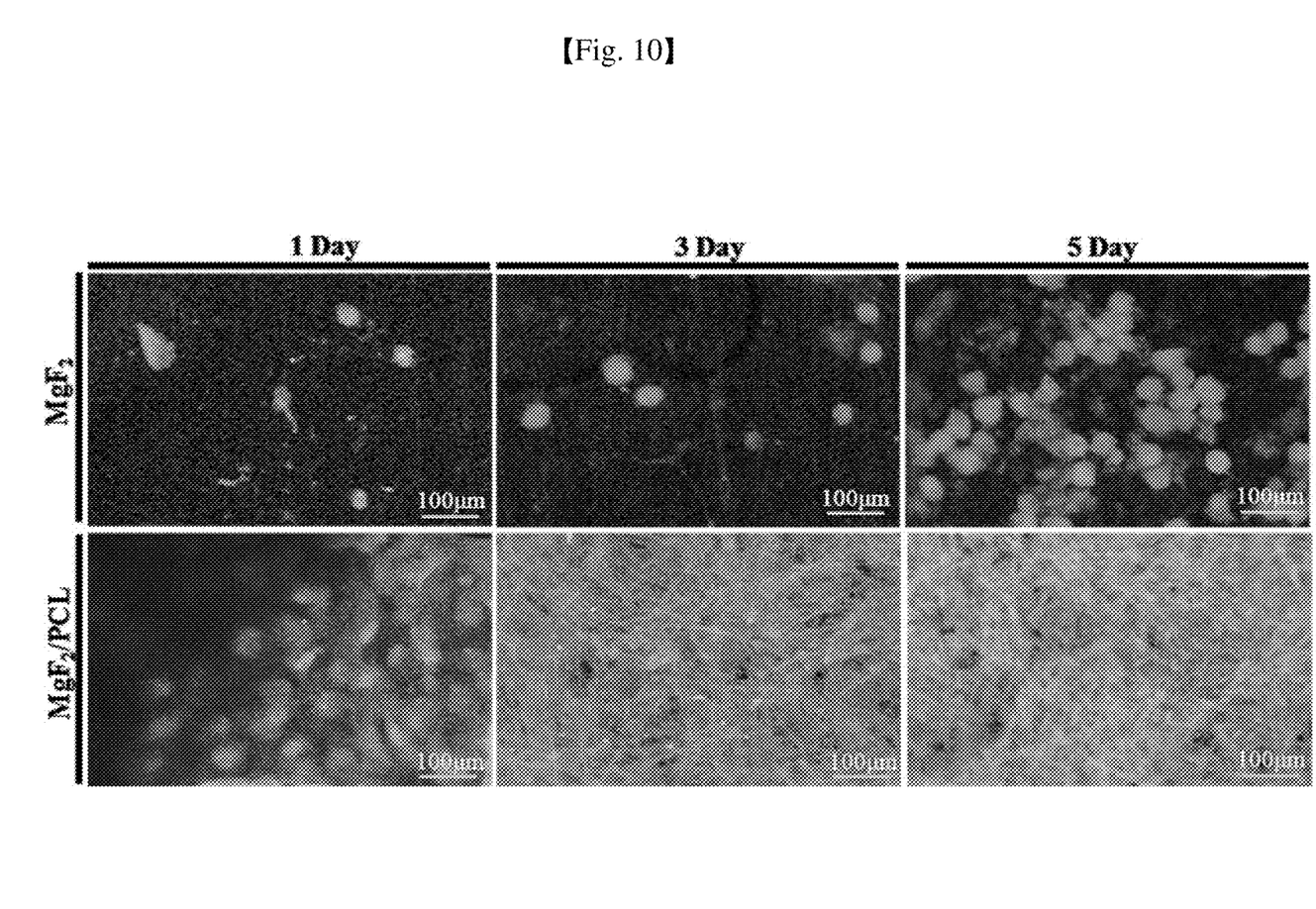
FIG. 10 shows $MgF_2$ and $MgF_2$/PCL coatings (a) cell proliferation behavior after incubation for 1, 3, and 5 days and (b) cell adhesion behavior after seeding for 4 hours.

FIG. 10 shows $MgF_2$ and $MgF_2$/PCL coating (a) cell proliferation behavior after incubation for 1, 3, and 5 days and (b) cell adhesion behavior after 4 h seeding.

Quality proliferation of the MC3T3-E1 cells on the $MgF_2$ and $MgF_2$/PCL coating was examined by confocal imaging (FIG. 10). The images demonstrate that cells attached and continuously proliferated on both coatings. The surfaces of both coatings supported growth of cells and metabolic activity thereof. It was revealed that the cell density was highest for the MgF$_2$/PCL coating after 5 days culture. The proliferation results showed that more cells seemed to be attached to MgF$_2$/PCL than the MgF$_2$ coating after 1, 3 and 5 days of incubation.

In conclusion, it is also indicated that the MgF$_2$/PCL coating had higher cell density and more cell spreading compared to MgF$_2$ coating after incubation for 1, 3, and 5 days.

The proliferation data correlated with the pH results showing that MgF$_2$ coating might influence significant cell growth and morphology as pH increases continuously with time (FIG. 6A). The post treatment of PCL on fluoride treated Mg substrate might cause topographical simulation and boost focal cell adhesion owing to its superior hydrophilicity (FIG. 4B). The cell proliferation and cell adhesion results were consistent with cell viability showing that MgF$_2$/PCL coatings support cell growth and proliferation, and exhibit better biocompatibility.

The present invention relates to a method for preparing a dual-layer coating on magnesium alloy with fluoride and biopolymer coatings, wherein the dual-layer MgF$_2$/PCL coating exhibits improved corrosion resistance as compared to fluorine-coated samples and uncoated Mg samples, and exhibits excellent cell viability, cell adhesion and cell proliferation, thus being useful as an implant for fixing bones with improved corrosion resistance.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for preparing a dual-layer coating on magnesium alloy comprising:
    polishing a surface of a magnesium alloy;
    treating the polished magnesium alloy with fluoride to prepare a magnesium fluoride coating layer on the magnesium alloy; and
    coating the fluoride coating layer with a biopolymer solution to form a biopolymer layer.

2. The method according to claim 1, wherein the magnesium alloy comprises zinc, zirconium and magnesium.

3. The method according to claim 1, wherein the fluoride is hydrofluoric acid.

4. The method according to claim 1, wherein the polymer is selected from the group consisting of polyetherimide (PEI), polycaprolactone (PCL), chitosan, polylactic acid (PLA), polyglycolic acid (PGA), a poly-ε-caprolactone-lactic acid copolymer (PCLA), a poly-ε-caprolactone-glycolic acid copolymer (PCGA), a polylactic acid-glycolic acid copolymer (PLGA), polyethylene glycol (PEG), polydioxanone (PDO), polytrimethylene carbonate (PTMC), polyamino acid, polyanhydride, polyorthoester, polyphosphazene, polyiminocarbonate, polyphosphoester, polyhydroxyvalerate, a copolymer thereof and a mixture thereof.

5. The method according to claim 1, wherein the biopolymer solution is prepared by dissolving a biopolymer in dichloromethane.

6. The method according to claim 1, wherein the fluoride coating layer has a thickness of 1.2 to 3.2 μm.

7. The method according to claim 1, wherein the biopolymer coating layer has a thickness of 2.0 to 4.3 μm.

* * * * *